(12) United States Patent
Das et al.

(10) Patent No.: US 11,856,882 B2
(45) Date of Patent: Jan. 2, 2024

(54) AUTONOMOUS ROBOT SYSTEM FOR STEEP TERRAIN FARMING OPERATIONS

(71) Applicant: Kansas State University Research Foundation, Manhattan, KS (US)

(72) Inventors: Sanjoy Das, Manhattan, KS (US); Daniel Flippo, Manhattan, KS (US); Stephen M. Welch, Manhattan, KS (US)

(73) Assignee: Kansas Stte University Research Foundation, Manhattan, KS (US)

( * ) Notice: Subject to any disclaimer, the term of this patent is extended or adjusted under 35 U.S.C. 154(b) by 323 days.

(21) Appl. No.: 17/602,014

(22) PCT Filed: Apr. 10, 2020

(86) PCT No.: PCT/US2020/027642
§ 371 (c)(1),
(2) Date: Oct. 7, 2021

(87) PCT Pub. No.: WO2020/210607
PCT Pub. Date: Oct. 15, 2020

(65) Prior Publication Data
US 2022/0151135 A1      May 19, 2022

Related U.S. Application Data

(60) Provisional application No. 62/831,986, filed on Apr. 10, 2019.

(51) Int. Cl.
*A01B 69/04*       (2006.01)
*B64C 39/02*       (2023.01)
(Continued)

(52) U.S. Cl.
CPC ............ *A01B 69/008* (2013.01); *B64C 39/02* (2013.01); *G01C 21/3461* (2013.01);
(Continued)

(58) Field of Classification Search
CPC .. A01B 69/008; B64C 39/02; G01C 21/3461; G01C 21/3469; G05D 2201/0201
See application file for complete search history.

(56) References Cited

U.S. PATENT DOCUMENTS 6,128,574 A * 10/2000 Diekhans ............. G05D 1/0278
701/410
8,285,459 B2 * 10/2012 Diekhans ............... G01C 21/20
701/411

(Continued)

OTHER PUBLICATIONS

International Search Report and Written Opinion in corresponding PCT Application Serial No. PCT/US2020/027642, dated Jun. 29, 2020.

*Primary Examiner* — Luis A Martinez Borrero
(74) *Attorney, Agent, or Firm* — Hovey Williams LLP

(57) ABSTRACT

An autonomous farming system (26) comprising one or more ground-based drones (10) and one or more unmanned aerial vehicles (12), whose routes through a field are optimized by an autonomous farming control system (30) that utilizes linearly constrained integer quadratic programming. The farming system (26) is particularly suited for farming steep terrain that is not accessible to conventional farming equipment.

20 Claims, 6 Drawing Sheets

(51) Int. Cl.
*G01C 21/34* (2006.01)
*G05D 1/10* (2006.01)

(52) U.S. Cl.
CPC ......... *G01C 21/3469* (2013.01); *G05D 1/101* (2013.01); *G05D 2201/0201* (2013.01)

(56) References Cited

U.S. PATENT DOCUMENTS

| | | | | |
|---|---|---|---|---|
| 8,898,000 B2* | 11/2014 | Mcaree | .................. | E02F 9/262 701/25 |
| 9,464,902 B2* | 10/2016 | Isler | ...................... | G01C 21/005 |
| 9,756,773 B1 | 9/2017 | Barbosa et al. | | |
| 9,756,774 B1 | 9/2017 | Wilson | | |
| 10,296,005 B2* | 5/2019 | Cantrell | ............... | G05D 1/0094 |
| 10,791,665 B2* | 10/2020 | Miyake | ................... | A01G 23/02 |
| 10,827,672 B2* | 11/2020 | Cutter | .................... | A01C 21/005 |
| 11,001,380 B2* | 5/2021 | Nahuel-Andrejuk | .......................... | G01D 21/00 |
| 11,059,582 B2* | 7/2021 | Nahuel-Andrejuk | .......................... | G01D 21/02 |
| 11,129,323 B2* | 9/2021 | Green | ................... | G05D 1/0219 |
| 11,420,770 B2* | 8/2022 | Ahmed | .................... | H04N 7/08 |
| 2003/0164794 A1* | 9/2003 | Haynes | ............... | H04B 7/18504 342/353 |
| 2004/0193349 A1* | 9/2004 | Flann | ................... | G05D 1/0274 701/50 |
| 2006/0282467 A1* | 12/2006 | Peterson | ............... | G06Q 50/02 |
| 2007/0271002 A1* | 11/2007 | Hoskinson | ........... | G05D 1/0291 700/245 |
| 2010/0076640 A1* | 3/2010 | Maekawa | ............. | G05D 1/0217 701/25 |
| 2011/0068224 A1* | 3/2011 | Kang | .................... | B64C 39/024 244/116 |
| 2011/0153172 A1* | 6/2011 | Anderson | ............ | A01D 34/008 701/50 |
| 2012/0101725 A1* | 4/2012 | Kondekar | ............ | A01B 79/005 701/445 |
| 2012/0101784 A1* | 4/2012 | Lindores | ............... | A01B 79/005 703/2 |
| 2013/0231855 A1* | 9/2013 | Mcaree | ................... | E02F 9/262 701/301 |
| 2014/0024313 A1* | 1/2014 | Campbell | ............ | H04B 1/3822 455/41.2 |
| 2015/0070188 A1* | 3/2015 | Aramburu | ............ | A01G 25/167 340/870.02 |
| 2015/0310721 A1* | 10/2015 | Johnson | ................ | G06F 3/0484 340/540 |
| 2015/0319913 A1* | 11/2015 | Foster | .................. | G05D 1/0217 701/26 |
| 2015/0379702 A1* | 12/2015 | Ulman | ................... | H04N 25/00 348/207.1 |
| 2016/0018224 A1* | 1/2016 | Isler | ..................... | G05D 1/0217 701/25 |
| 2016/0082772 A1* | 3/2016 | Biderman | ................ | B60K 7/00 301/6.5 |
| 2016/0146611 A1* | 5/2016 | Matthews | ............ | A01B 79/005 701/533 |
| 2016/0157414 A1* | 6/2016 | Ackerman | ........... | A01B 69/008 701/25 |
| 2016/0196755 A1* | 7/2016 | Navot | ................... | B64C 39/024 701/4 |
| 2017/0131718 A1* | 5/2017 | Matsumura | ............. | G05D 1/02 |
| 2017/0258005 A1* | 9/2017 | Cutter | .................. | A01B 79/005 |
| 2017/0334560 A1 | 11/2017 | O'Connor et al. | | |
| 2018/0074499 A1* | 3/2018 | Cantrell | ............... | G05D 1/0094 |
| 2018/0156770 A1 | 6/2018 | Saez et al. | | |
| 2018/0359904 A1* | 12/2018 | Foster | .................. | G05D 1/0217 |
| 2018/0359906 A1* | 12/2018 | Foster | .................. | A01B 69/008 |
| 2019/0129435 A1* | 5/2019 | Madsen | ................. | G05D 1/0246 |
| 2019/0146513 A1* | 5/2019 | Tomita | ................. | G05D 1/0088 701/50 |
| 2019/0286151 A1* | 9/2019 | Palanisamy | ...... | G08G 1/096816 |
| 2019/0289770 A1* | 9/2019 | Wolters | ................ | G05D 1/0219 |
| 2020/0089241 A1* | 3/2020 | Kao | .................... | G05D 1/0217 |
| 2021/0333795 A1* | 10/2021 | Fitch | ................... | G05D 1/0217 |
| 2023/0304818 A1* | 9/2023 | Madsen | ................. | G01C 21/30 701/41 |

* cited by examiner

AUTONOMOUS ROBOT SYSTEM FOR STEEP TERRAIN FARMING OPERATIONS

CROSS-REFERENCE TO RELATED APPLICATIONS

This application is the U.S. National Stage of International Patent Application No. PCT/US2020/027642, filed Apr. 10, 2020, which claims the benefit of U.S. Provisional Patent Application No. 62/831,986, filed Apr. 10, 2019, entitled AUTONOMOUS ROBOT SYSTEM FOR STEEP TERRAIN FARMING OPERATIONS, each of which is incorporated by reference herein in its entirety.

STATEMENT REGARDING FEDERALLY SPONSORED RESEARCH OR DEVELOPMENT

This invention was made with government support under grant number 2018-67021-27415 awarded by the U.S. Department of Agriculture. The government has certain rights in the invention.

BACKGROUND OF THE INVENTION

Field of the Invention

The present invention is generally directed toward a system of autonomous robots that can perform farming operations on land that is suitable for crop production in all regards except that it is too steep for large combines, tractors, and other equipment used in conventional farming on flat ground. The system of robots includes one or more ground mobile robots (drones) and one or more unmanned aerial vehicles (UAVs) that are operable to service the drones. The present invention also comprises a framework for optimal route planning of the one or more drones and UAVs.

Description of the Prior Art

According to United Nations projections, global population is expected to reach an estimated 10 billion people by the year 2050. Ensuring an adequate food supply for the growing population is a pressing problem. Efforts are ongoing to find ways of increasing crop yield, and especially grain yield, on existing farmland. However, an alternate solution is to find ways of planting and harvesting farmland that is presently considered unsuitable for crop production due to its steep terrain rendering it inaccessible to conventional farm equipment.

Seeding flat planting sites involves sprinkling seeds in parallel rows that are usually regularly spaced. Conventional farm equipment for planting and harvesting often comprises tractors weighing several tons and multi-row planters and combines. Such large implements are incapable of accessing steep, but otherwise arable, terrain. Smaller farming equipment may possess certain advantages over conventional equipment; however, the nature of the terrain may render it unsafe for humans to be onboard for the purpose of operating the equipment.

Work has been progressing in the area of autonomous vehicles for farming operations. However, such vehicles are not necessarily configured for steep terrain operations, and thus, their utility is limited to conventional farming on flat ground. Accordingly, a need exists in the art for autonomous farming systems that are capable of farming steep terrain that is presently considered to be unsuitable for crop production.

SUMMARY OF THE INVENTION

According to one embodiment of the present invention there is provided a method of autonomously farming a field having steep terrain. In particular, at least a portion of the field upon which the farming operating is performed has a grade of at least 10%. The method comprises performing a farming operation, such as planting, harvesting, or fertilizing, within the field using at least one ground-based drone. The method also comprises servicing the at least one drone with at least one unmanned aerial vehicle (UAV) while the at least one ground-based drone is within the field. In certain embodiments, multiple ground-based drones may be serviced by a single UAV. The at least one drone and at least one UAV at least intermittently or periodically communicate at least one of an amount of energy used and an amount of time taken by the at least one drone and the at least one UAV to traverse between at least two sites within the field to an autonomous farming control system. The autonomous farming control system generates a time and/or energy optimized route plan for the at least one drone and the at least one UAV within the field using linearly constrained integer quadratic programming. The autonomous farming control system then communicates instructions to the at least one drone and the at least one UAV for carrying out the optimized route plans, which are then executed by the at least one drone and the at least one UAV.

According to another embodiment of the present invention there is provided a system for autonomous farming. The system comprises at least one ground-based drone and at least one unmanned aerial vehicle (UAV) configured to service the at least one drone. The system further comprises an autonomous farming control system that includes a processor and wireless communication equipment configured to permit communication between the at least one ground-based drone and/or the at least one to unmanned aerial vehicle and/or the autonomous farming control system. The autonomous farming control system is configured to (a) receive information regarding the topography of a field of arable land to be farmed and at least one physical parameter associated with the at least one drone and the at least one UAV; (b) receive information from the at least one drone and the at least one UAV regarding at least one of an amount of energy used and an amount of time taken by the at least one drone and the at least one UAV to traverse between at least two planting sites; (c) use linearly constrained integer quadratic programming to generate a time and/or energy optimized route plan for the at least one drone and the at least one UAV within the field; and (d) transmit the optimized route plan to the at least one drone and the at least one UAV using the wireless communication equipment.

According to still another embodiment of the present invention there is provided a method of autonomous farming using at least one ground-based drone and at least one unmanned aerial vehicle (UAV). The method comprises inputting information regarding the topography of a field of arable land to be farmed into an autonomous farming control system. The information includes the identification of a plurality of planting sites within the field. Information is also transmitted from the at least one drone and the at least one UAV to the autonomous farming control system that comprises (a) at least one of an amount of energy used and an amount of time taken by the at least one drone to traverse between planting sites p1 and p2 within the field, and (b) at least one of an amount of energy used and an amount of time taken by the at least one UAV to traverse between rendezvous sites x1 and x2 within the field. The various pieces of information described above are then converted, within one or more low rank update modules of the autonomous farming control system (that are of rank-1 when the information is transmitted by the at least one drone and the at least one UAV at every planting site), into distance matrices $D_G$ and $D_A$. The distance matrices $D_G$ and $D_A$ and at least one physical parameter associated with the at least one drone and the at least one UAV are input into a linearly constrained integer quadratic programming (LCIQP) module. A time and/or energy optimized route plan for the at least one drone and the at least one UAV is then output from the LCIQP module. Instructions are transmitted to the at least one drone and the at least one UAV for following the time and/or energy optimized route plans.

DETAILED DESCRIPTION OF THE PREFERRED EMBODIMENT

Certain embodiments of the present invention are directed toward apparatus and methods of planting and/or harvesting farmland having terrain that is too steep for conventional farming operations. However, the apparatus and methods described herein can also be used on traditional shallow or flat farmland as well. Accordingly, the scope of the present invention should not be viewed as limited to steep terrain farming operations only. Embodiments of the present invention utilize a system of one or more ground mobile robots, or drones, that are serviced by one or more unmanned aerial vehicles, UAVs. The UAVs can service the drones by replenishing consumables necessary for drone operation and offloading harvested crops. In particular embodiments, the drones are utilized to resupply seed, fertilizers, pesticides, batteries, or fuel to the drones so that the drones can continuously operate within the field without being taken out of service for such operations. Likewise, the UAVs can be used to offload harvested grain, again, so that the drones need not be taken out of the field when their onboard storage bins are full. In addition, certain methods according to the present invention may also comprise inserting the drones into the field to be cultivated using a UAV and/or removing the drone from the field using a UAV once the farming operation has been completed.

Unlike conventional farm implements that can plant and/or harvest wide swaths of farmland at a time, the drones for use with certain embodiments of the present invention are much smaller in size permitting them to more successfully operate on steep terrain. For this reason, it becomes important to operate the drones and UAVs as efficiently as possible in order to compete economically with conventional farming operations. Thus, certain embodiments of the present invention provide methods of optimal route planning for the drones working within the field and the UAVs that rendezvous with the drones to resupply their consumables (e.g., seed, fertilizer, batteries, and/or fuel), or to offload harvested crops from the air.

Figure 1:
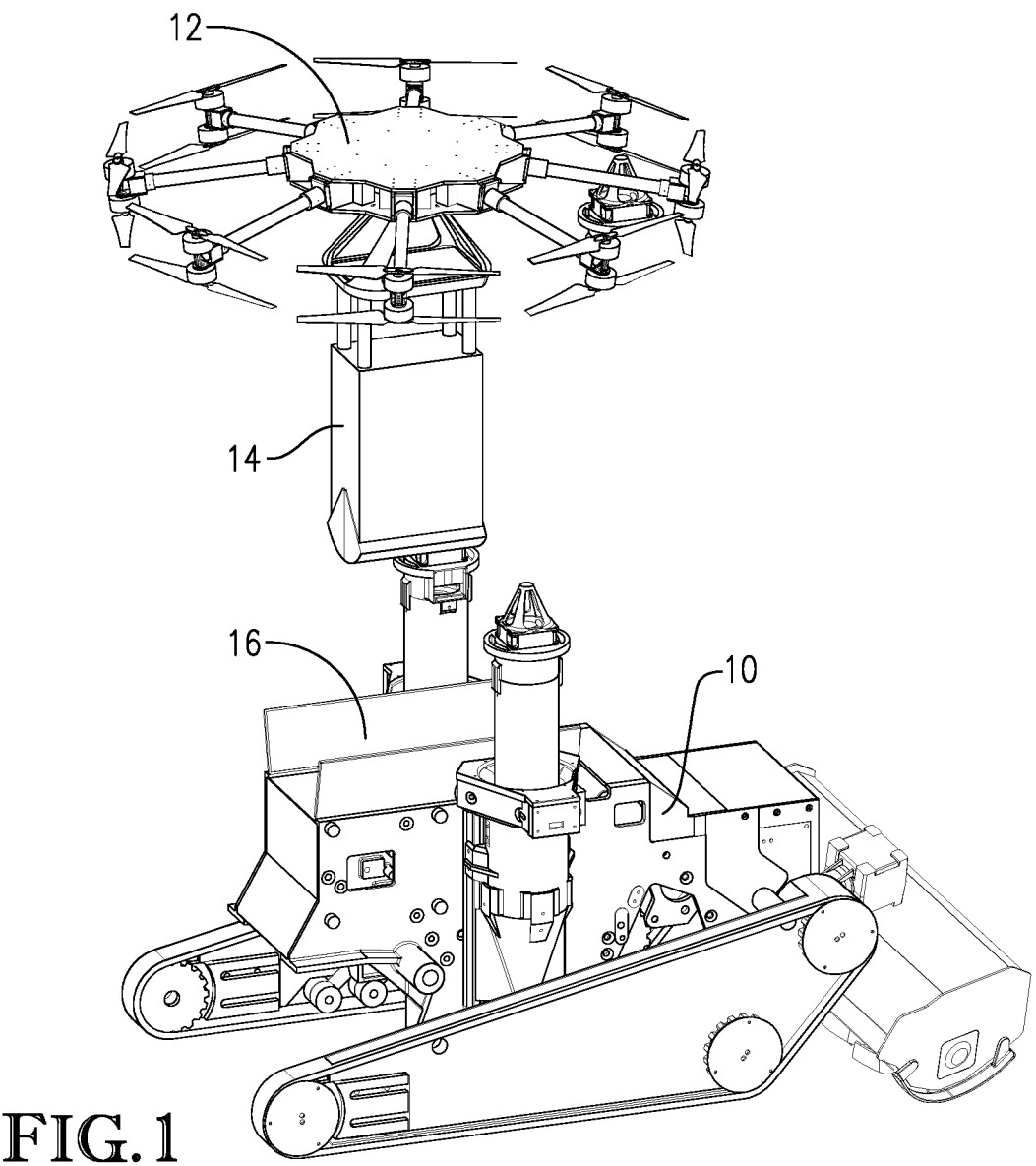
FIG. 1 is an illustration of an exemplary ground-based drone that may be used in embodiments of the present invention.

In one embodiment of the present invention, a system of autonomous robots are provided that are capable of planting seeds, providing for crop management, and/or harvesting crops, especially small grain crops such as wheat, on steep terrain that is presently unsuitable for farming operations or inaccessible by conventional combines, tractors and other farming equipment. Such terrain typically has significant sections having a slope of up to 30 degrees. In certain embodiments, at least 30%, 40%, 50%, 60%, or 70% of the field comprises land having a slope or grade of at least 10%, 15%, 20%, 25%. The system comprises a plurality of ground-based mobile robots, also referred to herein as drones, that perform planting, crop management, and/or harvesting operations. In certain embodiments, the drones may be battery powered; however, it is also within the scope of the present invention for the drones to comprise internal combustion engines. The drones are serviced by one or more unmanned aerial vehicles, UAVs, that can replenish the drones configured for planting with seed, replace the drone batteries, or refuel drones powered by internal combustion engines. Crop management drones can be configured to apply water, fertilizer, or pesticides, for example, to growing crops. These management drones can also have their supplies replenished from the air. Harvesting drones may be configured to have their harvested crops, especially grain, offloaded by a UAV when their internal storage bins are full so that the drones can remain working in the field and not be taken out of the field for offloading. FIG. 1 depicts one such combination of drone 10 and UAV 12 that may be used in certain embodiments of the present invention. Exemplary devices are also described in U.S. Provisional Patent Application No. 62/869,296, filed Jul. 1, 2019, which is incorporated by reference herein in its entirety.

The drones may be equipped with seed bins that are configured to receive seed from a UAV hovering over it. FIG. 1 illustrates an exemplary UAV 12 equipped to deliver seed to a drone 10. In particular, the UAV comprises a bulk product handling system 14 that can be flown into a hovering position over the drone's seed bin 16. Once in position, seed can be transferred from the UAV's bulk product handling system 14 to the drone's seed bin 16. Such drone and UAV can be adapted for any particular farming operation, such as applying fertilizers or pesticides to growing crops. If applying granular fertilizers or pesticides, the UAV can be configured to transfer the granules from its storage bin into the drone's bin, much like what is depicted in FIG. 1. If the drone is applying a liquid fertilizer or pesticide, the UAV can be equipped with an onboard liquid tank and contain a boom or other similar structure that can be extended and mated with receiving structure on the drone for transfer of the liquid into the drone's onboard liquid tank. If harvesting crops, the drone may be configured with a removable bin that can be picked up by the UAV and replaced with an empty bin.

Figure 2:
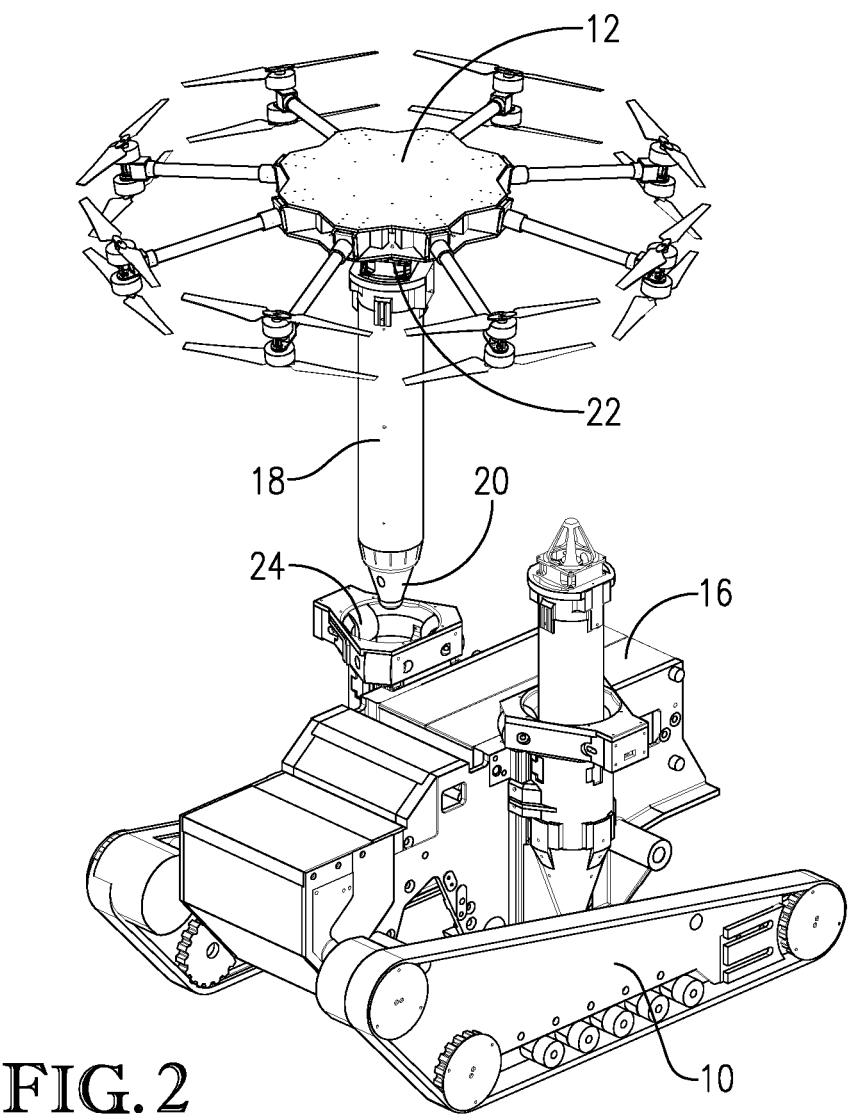
FIG. 2 is a depicts the servicing of a ground-based drone with a UAV according to an embodiment of the present invention.

FIG. 2 illustrates an exemplary UAV 12 equipped to change battery packs 18 carried by the drone 10. In the illustrated embodiment, the battery pack 18 is generally cylindrical with cone-shaped couplings 20 secured to each end. The battery pack is transported by the UAV's coupling mechanism 22 into position over the drone's battery compartment 24, lowered into position, and then decoupled from the UAV 12. The UAV 12 may also utilize the same coupling mechanism 22 to retrieve a depleted battery pack 18 from the drone 10 for recharging. In this manner, the drones 10 can operate nearly continuously and do not need to be removed from the fields once inserted. Insertion of the drones 10 into the fields can also be accomplished by the UAVs 12 or by other capable aerial support vehicle. If appropriate, the drones 10 may also be retrieved from the fields following completion of their respective planting or harvesting tasks by a UAV 12.

The UAVs 12 may also be equipped with pinpoint tracking systems. In certain embodiments, the pinpoint tracking systems use GPS to locate the drones 10, and then, when in range, a special approach light system is used to pinpoint which battery compartment 24 or seed bin 16 the UAV should settle on.

In certain embodiments, the autonomous farming system further comprise an autonomous farming control system that includes a processor and wireless communication equipment configured to permit communication between the at least one ground-based drone and/or the at least one unmanned aerial vehicle and/or the autonomous farming control system. The wireless communication equipment may comprise any wireless transmitters and receivers known to those of skill in the art, including but not limited to various radio communications equipment such as Wi-Fi systems, cellular systems, Bluetooth systems, and the like. The processor may be a microprocessor with associated memory for storing and performing computer-executable instructions such as those described herein.

Figure 3:
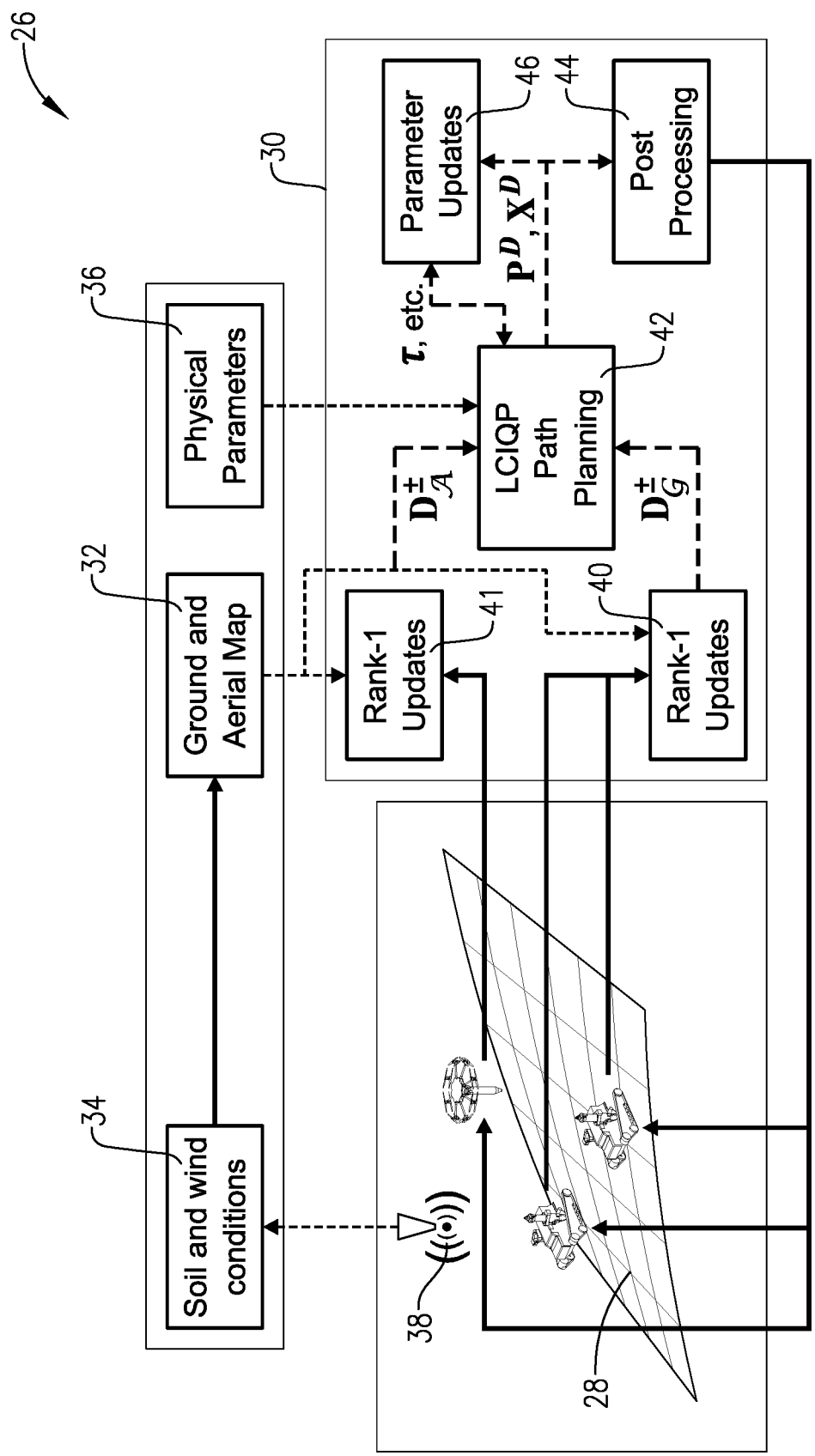
FIG. 3 is a diagram illustrating the connectivity and functionality of an autonomous farming control system according to an embodiment of the present invention.

Turning to FIG. 3, an exemplary autonomous farming system 26 is schematically depicted. System 26 comprises drones 10 that are serviced by UAV 12 and operate within a field 28 of arable land. System 26 comprises control system 30 that is configured to receive certain data that may or may not be collected and transmitted in real time. Examples of non-real time data include information regarding the topography of the field, such as ground and/or aerial maps 32, field conditions 34 (such as type of soil, average moisture content, wind conditions, etc.), and various physical parameters 36 associated with the drone 10 and UAV 12 such as at least one of a drone weight, a drone seed capacity, a UAV weight, a UAV seed capacity, and an amount of seed required per planting site. Data regarding field conditions 34 can also be gathered and transmitted to control system 30 in real time through the use of sensors 38 that may be located within the field or carried by drones 10 or UAV 12.

The control system 30 is also configured to receive information from drones 10 and UAV 12 regarding at least one of an amount of energy used and an amount of time taken by the at least one drone and the at least one UAV to traverse between at least two sites. This data may be transmitted and received in real time, and thus, such information can be continuously communicated to control system 30. In certain embodiments, the information received from the drones 10 and UAV 12 is received by one or more low rank updates modules 40, 41 of control system 30. If the drone 10 or UAV 12 is configured to transmit to the control system 30 the amount of energy expended or time taken in going from one planting site to an adjacent planting site, the low rank updates modules 40, 41 are configured to perform rank-1 updates. However, if the drone 10 or UAV 12 is configured to transmit the amount of energy expended or time taken in traversing between odd numbered planting sites, for example, the low rank updates modules 40, 41 are configured to perform rank-2 updates, and so forth. It is noted that although the following description may refer to "rank-1 updates", it should be understood that such modules may be configured to perform updates with rank higher than one. As illustrated in FIG. 3, control system 30 comprises two rank-1 updates modules, one 40 configured to receive data from drones 12, and one 41 configured to receive data from UAV 12. Each of modules 40, 41 is also configured to receive the real time and/or non-real time data regarding field topography, field conditions and robot physical parameters. As described in greater detail below, the output of the rank-1 updates modules 40 is input into a linearly constrained integer quadratic programming (LCIQP) module 42 that uses linearly constrained integer quadratic programming to generate a time and/or energy optimized route plan for the drones 10 and the UAV 12 within the field 28. The output from the LCIQP module 42 is converted into instructions that are executable by drones 10 and UAV 12 within a post-processing module 44 and then transmitted to drones 10 and UAV 12 via the wireless communication equipment.

In certain embodiments, the rank-1 updates module 40 is configured to receive information from the drone as to energy used and/or time taken to traverse two planting sites along with information regarding the topography of the field 28 (e.g., a ground map) and convert the information into a distance matrix $D_G$. As used herein, the term "planting site" refers to a location within the field where a seed has been deposited. The rank-1 updates module 41 is configured to receive information from the UAV as to energy used and/or time taken to traverse two rendezvous sites, at which the UAV meets up with a drone, along with information regarding the topography of the field (e.g., aerial map including elevational data) and convert the information into a distance matrix $D_A$. As used herein, the term "rendezvous site" refers to a location within the field where a ground-based drone and a UAV rendezvous so that the UAV may service the drone. A rendezvous site may coincide with a planting site, but this need not always be the case. These distance matrices are not direct distance metrics, but rather mathematical expressions having a relationship to the actual distances traversed by the drone and UAV. In certain embodiments, the LCIQP module is configured to generate the optimized route plan for the at least one drone and the at least one UAV using the distance matrices $D_G$ and $D_A$ and at least one physical parameter associated with the at least one drone and the at least one UAV, such as those mentioned previously.

In certain embodiments, the output from the LCIQP module 42 comprises a planting matrix $P^D$ and a rendezvous matrix $X^D$. These matrices generally comprise the route planning instructions for the various drones 10 and UAVs 12, but in a binary form. The matrices $P^D$ and $X^D$ are input to a post-processing module 44 that converts the binary instructions into instructions that can be executed by the drones 10 and UAVs.

Because the matrices $P^D$ and $X^D$ are in binary form, a parameter updates module 46 can receive output from the LCIQP module 42 and apply mathematical corrections to the matrices and feed the corrected data back to the LCIQP module. In so doing, the feedback provided by the parameter updates module 46 improves the accuracy of the matrices output from the LCIQP module 42.

In certain embodiments, the methods for route planning comprise an algorithm that is implemented on a fully connected recurrent neural network that can be viewed as a primal-dual extension of a Hopfield network. These networks, for example, may be burned into field programmable gate array (FPGA) chips that can be carried by the drones and/or UAVs or a command and control center that remotely controls the guidance of the drones and/or UAVs. The processors can receive inputs associated with, for example, seed weight, coordinates, and distances, and identify the optimal ground and aerial routes to be taken by the drones and UAVs and rendezvous locations for resupplying the drones with seed, batteries, and/or fuel.

Methods of autonomous farming using at least one ground-based drone 10 and at least one UAV 12 are provided that comprise the inputting of various bits of real time and/or non-real time information into the autonomous farming control system 30. Non-real time information is input to the autonomous farming control system 30 regarding the topography of the field (ground and/or aerial maps, for example). This information includes the identification of a plurality of planting sites within the field. Other information can also be input into the control system 30 including real time information regarding soil and wind conditions in the field and/or non-real time information regarding a physical parameter associated with the at least one drone an the at least one UAV.

Real time information is also transmitted to the autonomous farming control system 30 by the drones 10 and UAVs 12. This information comprises at least one of an amount of energy used and an amount of time taken by the at least one drone to traverse between planting sites p1 and p2 within the field, and at least one of an amount of energy used and an amount of time taken by the at least one UAV to traverse between rendezvous sites x1 and x2 within the field. It is noted that sites p1, p2, x1 and x2 may be independently chosen, and, therefore, it is possible for one or more of the planting sites p(i) to also be a rendezvous site x(i).

The rank-1 updates modules 40, 41 convert the information received from the drone and UAV and the field topography information into distance matrices $D_G$ and $D_A$. These distance matrices, along with at least one physical parameter associated with the at least one drone and the at least one UAV are input into the LCIQP module 42. Time and/or energy optimized route plans for the at least one drone and the at least one UAV are output from the LCIQP module 42 as described above. Finally, route plans generated within the LCIQP are transmitted to the at least one drone and the at least one UAV by the wireless communication system, preferably after having undergone post-processing within module 44.

Embodiments of the present invention provide a framework for multi-robot route planning for selective crop operations in steep terrain with slopes of up to 30°. The team of robots includes at least one ground autonomous vehicles (drones) for crop seeding or harvesting, for example, as well as at least one UAV to service the at least one drone, such as to replenish the drones with seed supplies, batteries, or fuel.

The problem of route planning of the drones and the UAV(s) has been formulated in terms of integer quadratic programming with linear constraints. The algorithm described below is capable of being implemented on a fully connected recurrent neural network, that can be viewed as an extension of a Hopfield network.

Generally, seeding flat planting sites involves sprinkling seeds in parallel rows that are usually regularly spaced. However, such a pattern may not necessarily apply to steep, undulating landscapes. Although the present discussion planting sites are discretized into R rows and C columns, the terrain conditions introduce significant differences in the physical distances between adjacent pairs of points.

Figure 4A:
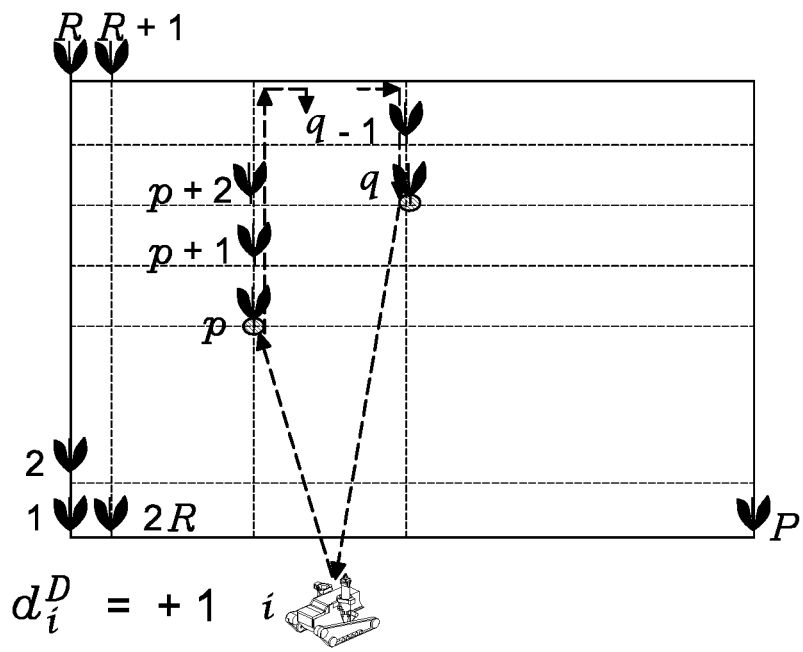
FIG. 4a is a schematic illustration of a positive direction route plan for a ground-based drone.
Figure 4B:
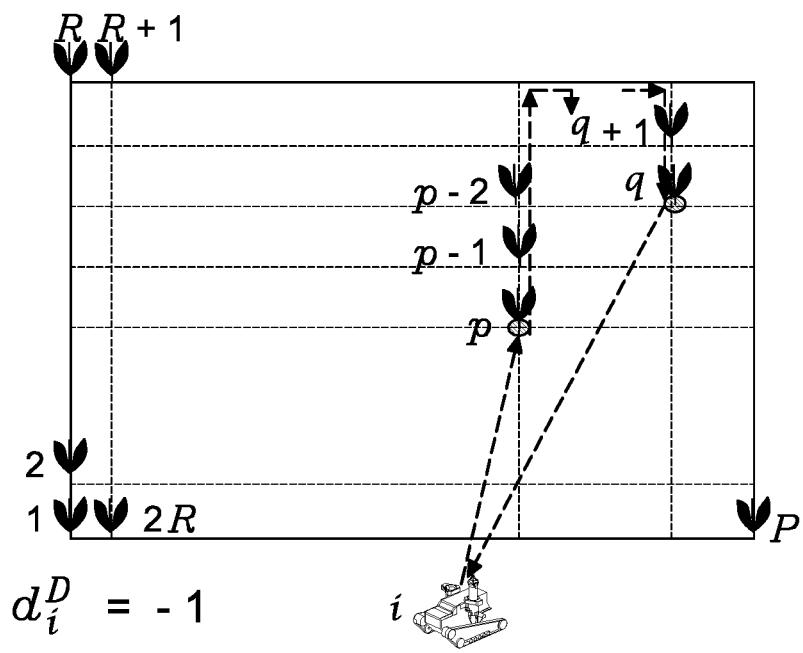
FIG. 4b is a schematic illustration of a negative direction route plan for a ground-based drone.
Figure 4C:
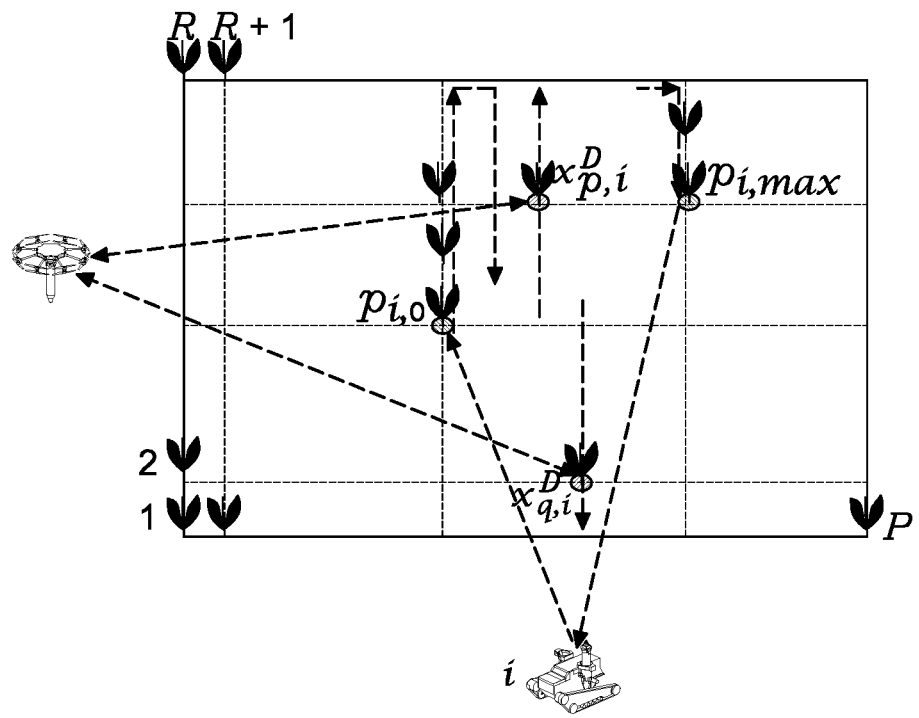
FIG. 4c is a schematic illustration of the interaction between a ground-based drone and UAV including various planting and rendezvous sites.

For convenience, it is assumed that each discrete point in the two-dimensional grid requires an equal amount of seed, $s^P$, to be delivered by the drone. The large variability in the physical distances that the landscape is addressed below. The two-dimensional points are indexed p=1, 2, . . . , P, where P=R×C. Furthermore, starting with a corner point, p=1, in column 1 of row 1, the plant indices are incremented by 1 going forward each odd numbered row but decremented in case of even numbered rows. Denoting the set of planting points by $\mathcal{P}=\{1, 2, \ldots, P\}$, and the set of drones as $\mathcal{D}=\{1, 2, \ldots, D\}$ (D=|$\mathcal{D}$|), it can readily be seen that a drone's movement would be either along unit increments or along unit decrements of plant indices. FIGS. 4a-c illustrate this layout. FIG. 4a illustrates positive drone directions, and the top right schematic illustrates negative drone directions. FIG. 4b illustrates drone start and end locations (in the positive direction). The direction of any drone i∈$\mathcal{D}$ is denoted as $d_i^D=\pm 1$. The $i^{th}$ drone begins planting at point $p_{i,0}$ and ends its schedule at point $p_{i,max}$, ($p_{i,0}$, $p_{i,max}\in\mathcal{P}$), such that $p_{i,0}<p_{i,max}$ when $d_i^D=+1$ and $p_{i,0}>p_{i,max}$ when $d_i^D=-1$.

The ground "distance" between any pair of points p, q∈ $\mathcal{P}$ is denoted as $d_\mathcal{G}(p, q)$. This metric is proportional to the energy that a drone would use in moving from p to q with the constant of proportionality being conveniently treated as unity. Hence $d_\mathcal{G}(p, q)$ must take into account not only elevation differences, but also ground and soil conditions, so that $d_\mathcal{G}(p, q) \neq d_\mathcal{G}(q,p)$. Although the term "distance" is used in this discussion, strictly speaking, $d_\mathcal{G}(p, q)$ is a Bregman divergence instead of an actual distance metric. During physical deployment of the drones, the distances are determined by means of a manifold learning algorithm that performs regular iterative updates as soil conditions change over time.

A. Constraints

In a slight misuse of notation, $p_{p,i}^D$ is defined to be a binary variable, with $p_{p,i}^D=1$ if drone i delivers seed to point p, and $p_{p,i}^D=0$ otherwise. All variables $p_{p,i}^D$ are arranged into a P×D binary matrix $P^D$. Since each planting site must be seeded by exactly one drone, $$P^D 1_D = 1_P. \qquad (1)$$

In the above expression and elsewhere herein, $1_Z$ denotes a Z×1 vector of all ones. In order to ensure that all drones are deployed, an additional constraint may be included, $$P^{D^T} 1_P \geq 1_D. \qquad (2)$$

The matrix $P^D$ is one of the decision variables of the route planning problem that is formulated below. Each column i of $P^D$ is the P×1 vector $p_i^D$. Denoting $x_{p,i}, p\in(p_{i,0}, p_{i,max})$ as the rendezvous points where the $i^{th}$ drone is replenished with seeds by the UAV, the P×D rendezvous matrix, $[X^D]_{p,i}=x_{p,i}^D$ is defined as the other decision variable. The direction vector $d^D$ whose $i^{th}$ element is defined as $[d^D]_i=d_i^D$.

Assuming that the $i^{th}$ drone begins with full capacity, so that its total weight is $w^D+s^D$, at each plant site, the weight drops by an amount $s^P$. The weight can never be lower than that of the empty drone, $w^D$. At each replenishment point, see FIG. 4c, the weight increases to $w^D+s^D$. A P×1 vector of weights, $w_i^D$ at each planting site for the $i^{th}$ drone is devised as follows. First consider the case when $d_i^D=+1$. Since the weight drop can neither be negative nor exceed the drone's capacity, $s^D$, the threshold operator thr(•) is used to restrict its arguments to lie in the interval $[0, s^D]$. Hence, the vector $w_i^D$ is equal to $(w^D+s^D)p_i^D-\text{thr}(s^PT_{P,P}^l p_i^D - \theta_i^D s^D T_{P,P}^l x_i^D) \circ p_i^D$. The quantity $\theta_i^D \in [0,1]$ in this expression is the ratio of the mean weight of seed dropped by the drone between two replenishments as a fraction of its capacity $s^D$. The negated last term $\text{thr}(s^PT_{P,P}^l p_i^D - \theta_i^D s^D T_{P,P}^l x_i^D) \circ p_i^D$ represents the vector of weight drops. Whence thr(z)=min(max(z, 0), $s^D$). The threshold operator yields the linear constraint, $$d_i^D = +1 \Rightarrow \begin{cases} s^P T_{P,P}^l p_i^D - \theta_i^D s^D T_{P,P}^l x_i^D \geq 0_P, \\ s^P T_{P,P}^l p_i^D - \theta_i^D s^D T_{P,P}^l x_i^D \leq s^D 1_P \end{cases}. \quad (3)$$

In a similar manner, $$d_i^D = -1 \Rightarrow \begin{cases} s^P T_{P,P}^u p_i^D - \theta_i^D s^D T_{P,P}^u x_i^D \geq 0_P, \\ s^P T_{P,P}^u p_i^D - \theta_i^D s^D T_{P,P}^u x_i^D \leq s^D 1_P \end{cases}. \quad (4)$$

In (3) and (4), $T_{P,P}^l$ and $T_{P,P}^u$ are P×P lower and upper triangular matrices.

B. Drone Cost Function

Combined with the linear constraints in (3) and (4), the weight vector $w_i^D$ of the $i^{th}$ drone can be simplified. When $d_i^D=+1$, $$w_i^D = w^D p_i^D (\theta_i^D s^D T_{P,P}^l x_i^D - s^P T_{P,P}^l p_i^D) \circ p_i^D. \quad (5)$$

In a similar manner, when $d_i^D=-1$, $$w_i^D = w^D p_i^D + (\theta_i^D s^D T_{P,P}^u x_i^D - s^P T_{P,P}^u p_i^D) \circ p_i^D. \quad (6)$$

Figure 5:
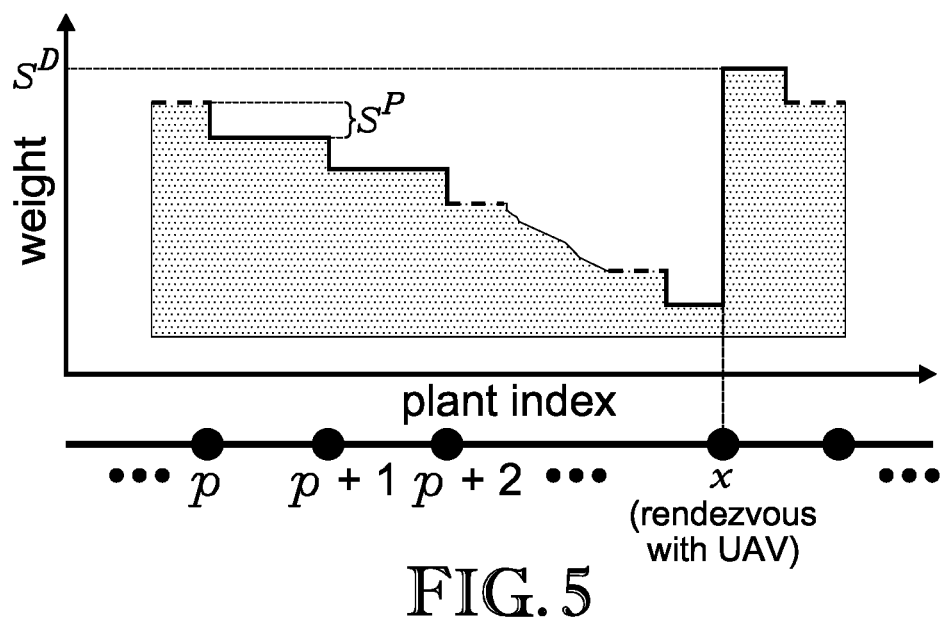
FIG. 5 is a chart showing weight as a function of plant index for a drone moving in the positive direction.

FIG. 5. illustrates this scheme. The chart of FIG. 5 illustrates weight as a function of plant index for a drone moving in the positive direction. The diagonal matrices $\mathbf{D}_G^+$ and $\mathbf{D}_G^-$ are defined as follows, $$[\mathbf{D}_G^+]_{pq} = \begin{cases} d_G(p,0), & q=p, p=P; \\ d_G(p,q+1), & q=p, p<P; \\ 0, & q \neq p \end{cases} \quad (7)$$

$$[\mathbf{D}_G^-]_{pq} = \begin{cases} d_G(0,q), & p=q, q=1; \\ d_G(p,q+1), & p=q, q>1; \\ 0, & p \neq q \end{cases} \quad (8)$$

When $d_i^D=+1$, the P×1 vector of distances traveled by the $i^{th}$ drone between the plant sites $p_{i,0}$, $p_{i,max}$ is $\mathbf{D}_G^+ w^D$. Likewise, when $d_i^D=-1$, the vector of distances is $\mathbf{D}_G^- w^D$. Assuming a proportional constant of $e^D=1$, the cost $\varphi_i(d_i^D, p_i^D, x_i^D)$ incurred by the $i^{th}$ drone is obtained according to the following expressions, $$\varphi_i(+1,p_i^D,x_i^D) = p_i^{D^T}(-s^P \mathbf{D}_G^+ \mathbf{T}_{P,P}^l) p_i^D + p_i^{D^T}(\theta_i^D s^D \mathbf{D}_G^+ \mathbf{T}_{P,P}^l) x_i^D + w^D 1_P^T \mathbf{D}_G^+ p_i^D. \quad (9)$$

$$\varphi_i(-1,p_i^D,x_i^D) = p_i^{D^T}(-s^P \mathbf{D}_G^- \mathbf{T}_{P,P}^u) p_i^D + p_i^{D^T}(\theta_i^D s^D \mathbf{D}_G^- \mathbf{T}_{P,P}^u) x_i^D + w^D 1_P^T \mathbf{D}_G^- p_i^D. \quad (10)$$

C. UAV Cost Function

Aerial distances between points $d_A$ (p, q) can be defined in a manner similar to ground distances, which are machine learnable Bregman divergences. The UAV whose weight is $w^U$ leaves its station with seed of weight $s^D$ to each location specified with a 1 in the $p_i^D$ of each drone i and returns empty. Define the vectors $\mathbf{d}_A^+, \mathbf{d}_A^-$ as, $$\begin{cases} \mathbf{d}_A^+ = [d_A(0,p)]_{p \in \mathcal{P}}, \\ \mathbf{d}_A^- = [d_A(p,0)]_{p \in \mathcal{P}} \end{cases}. \quad (11)$$

Hence, the cost of the UAV due to any drone i is, $$\varphi_i^D(d_i^D, p_i^D, x_i^D) = e^U(w^U+s^D) \mathbf{d}_A^{+T}(p_i^D \circ x_i^D) e^U + w^U \mathbf{d}_A^{-T}(p_i^D \circ x_i^D). \quad (12)$$

a. Linearly Constrained Integer Quadratic Programming

The 2P×P coefficient matrices are defined as follows, $$C_i^D = \begin{cases} s^P \begin{bmatrix} -T_{P,P}^l \\ T_{P,P}^l \end{bmatrix}, & d_i^D = +1; \\ s^P \begin{bmatrix} -T_{P,P}^u \\ T_{P,P}^u \end{bmatrix}, & d_i^D = -1 \end{cases} \quad (13)$$

$$C_i^U = \begin{cases} s^D \begin{bmatrix} T_{P,P}^l \\ -T_{P,P}^l \end{bmatrix}, & d_i^D = +1; \\ s^D \begin{bmatrix} T_{P,P}^u \\ -T_{P,P}^u \end{bmatrix}, & d_i^D = -1 \end{cases} \quad (14)$$

Additionally, the following vector is defined, $$s_i^D = s^D \begin{bmatrix} 0_P \\ 1_P \end{bmatrix}. \quad (15)$$

Using (13), (14), and (15), the constraints defined in (3) and (4) can be expressed succinctly as, $$C_i^D p_i^D + C_i^U x_i^D + s_i^D \leq 0_{2P}. \quad (16)$$

The quadratic and linear coefficient matrices, $Q_i^D$ and $R_i^{DU}$, as well as the constant coefficient vector, $r_i^D$, are defined in the following manner, $$Q_i^D = \begin{cases} -2e^D s^P \mathbf{D}_G^+ T_{P,P}^l, & d_i^D = +1; \\ -2e^D s^P \mathbf{D}_G^- T_{P,P}^u, & d_i^D = -1 \end{cases}. \quad (17)$$

$$R_i^{DU} = \begin{cases} e^D s^D \mathbf{D}_G^+ T_{P,P}^l, & d_i^D = +1; \\ e^D s^D \mathbf{D}_G^- T_{P,P}^u, & d_i^D = -1 \end{cases}. \quad (18)$$

$$r_i^D = \begin{cases} e^D s^D \mathbf{D}_G^+ T_{P,P}^l x_i^D + e^D(w^D+s^D) 1_P \mathbf{D}_G^+, & d_i^D = +1; \\ e^D s^D \mathbf{D}_G^- T_{P,P}^u x_i^D + e^D(w^D+s^D) 1_P \mathbf{D}_G^-, & d_i^D = -1 \end{cases}. \quad (19)$$

The expressions in (17), (18), and (19) can be combined with the ones that were obtained earlier in (9), (10), (11), and (12) for a more concise equation for the cost function, $$\varphi_i^D(d_i^D,p_i^D,x_i^D) = \tfrac{1}{2} p_i^{D^T} Q_i^D p_i^D + x_i^{D^T} R_i^{DU} p_i^D + r_i^{D^T} p_i^D. \quad (20)$$

Using (1), (16), and (20), the following LCIQP formulation is defined,
Minimize:

$$\Omega(d^D, P^D, X^D) = \quad (21)$$

-continued $$\sum_i \frac{1}{2} p_i^{D^T} Q_i^D p_i^D + \sum_i x_i^{D^T} R_i^{DU} p_i^D + \sum_i r_i^{U^T}(x_i^D \circ p_i^D) + \sum_i r_i^{D^T} p_i^D.$$

Subject to:

$$\begin{cases} C_i^D p_i^D + C_i^U x_i^D + s_i^D \le 0_{2P}, \\ P^D 1_D - 1_P = 0_P, \\ P^{D^T} 1_P \ge 1_D, \\ d_i^D \in \{0, 1\}, p_{p,i}^D \in \{0, 1\} \end{cases} \quad (22)$$

b. Recurrent Neural Network Implementation

With the LCIQP formulation involving all binary decision variables, optimal routes for drones and UAVs can be planned through a variety of algorithms including those that are readily available as commercial of-the-shelf software. Real-time route planning is accomplished by means of recurrent neural network hardware. The binary decision variables, $d_i^D$, $p_i^D$, $x_i^D$ are relaxed to lie anywhere in $[0,1]^D$, where D reflects the appropriate dimensionalities of the variables involved. The binary variables are retrieved from the outputs of neurons with saturating nonlinear transfer functions.

Simulations with two drones and a UAV are discussed below. All physical parameters used are provided in Table 1.

TABLE 1

| Symbol | $s^P$ | $s^D$ | $w^D$ | $e^D$ | $e^U$ |
|---|---|---|---|---|---|
| Value | 1.00 | 8.00 | 50.00 | 10.00 | 5.50 |

Figure 6:
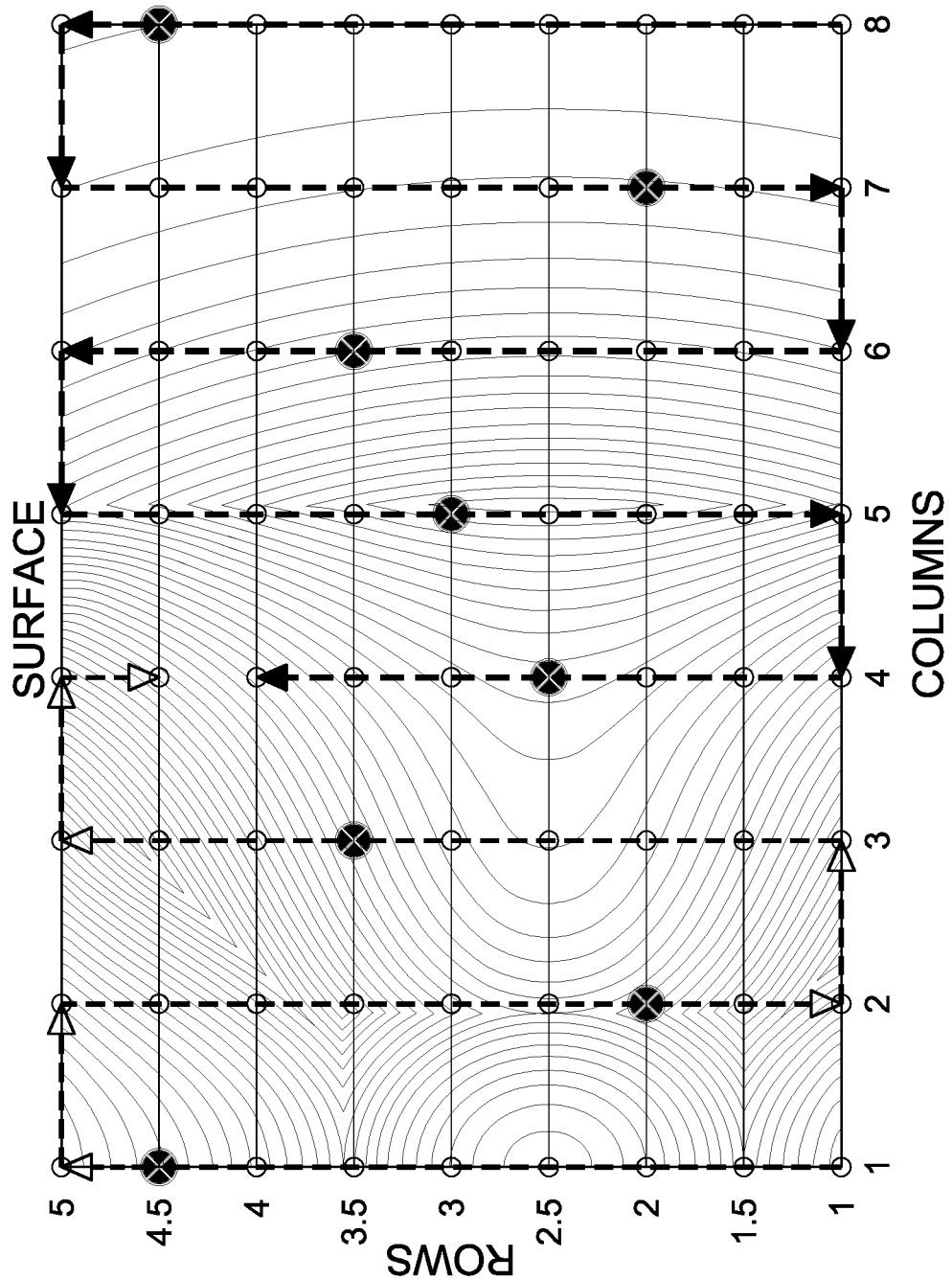
FIG. 6 is a schematic field layout used to simulate the paths of two drones traversing planting sites within a field having a portion with steep terrain.

The entire planting site was divided into R=10 rows and C=8 columns. The rows were regularly spaced 0.5 m apart, and the columns were spaced 1.0 m apart. However, the ground condition was not uniform. FIG. 6 shows the layout used in the simulations. The small, hollow circles are planting sites. The contours show how ground conditions varied spatially, with the slope of the terrain decreasing moving left to right. Given the direction of decreasing slope, moving a unit distance on the left side of the layout requires up to 3 times as much energy as moving a unit distance on the right side of the layout. The dashed arrows show the trajectory taken by the 1$^{st}$ drone (left) and the 2$^{nd}$ drone (right). Since the extra energy required in navigating the left region in the layout the 1$^{st}$ drone could cover 29 planting sites, whereas the 2$^{nd}$ drone, which was assigned an easier terrain, could cover 43 sites. The larger, filled circles are rendezvous points, where the UAV replenished the drones with seed supply.

We claim:

1. A method of autonomously farming a field having steep terrain comprising:
performing a farming operation within the field using at least one ground-based drone, at least a portion of the field upon which the farming operation is performed has a grade of at least 10%;
servicing the at least one drone with at least one unmanned aerial vehicle (UAV) while the at least one ground-based drone is within the field;
communicating at least one of an amount of energy used and an amount of time taken by the at least one drone and the at least one UAV to traverse between at least two sites within the field to an autonomous farming control system, the autonomous farming control system generating a time and/or energy optimized route plan for the at least one drone and the at least one UAV within the field using linearly constrained integer quadratic programming; and
communicating instructions to the at least one drone and the at least one UAV for carrying out the optimized route plans.

2. The method of claim 1, wherein the farming operation comprises planting seeds or harvesting grain.

3. The method of claim 1, wherein the servicing of the at least one drone comprises refueling the drone either by replacing a battery pack carried by the at least one drone or providing fuel for an internal combustion engine of the at least one drone.

4. The method of claim 1, wherein the servicing of the at least one drone comprises supplying the at least one drone with seeds.

5. The method of claim 1, wherein the servicing of the at least one drone comprises removing harvested grain from the at least one drone.

6. The method of claim 1, wherein at least a portion of the field has a grade of up to 30%.

7. The method of claim 1, wherein the autonomous farming control system is configured to take into account, when generating the optimized route plan of the at least one drone and the at least one UAV, one or more of the topography of the field, soil and/or wind conditions within the field, and at least one physical parameter associated with the at least one drone and the at least one UAV.

8. The method of claim 7, wherein the at least one physical parameter comprises at least one of a drone weight, a drone seed capacity, a UAV weight, a UAV seed capacity, and an amount of seed required per planting site.

9. The method of claim 1, wherein the instructions communicated to the at least one UAV includes coordinates for the UAV to rendezvous with he at least one drone to perform the servicing of the drone.

10. A system for autonomous farming comprising:
at least one ground-based drone;
at least one unmanned aerial vehicle (UAV) configured to service the at least one drone; and
an autonomous farming control system comprising a processor and wireless communication equipment configured to permit communication between the at least one ground-based drone and/or the at least one unmanned aerial vehicle and/or the autonomous farming control system,
the autonomous farming control system being configured to—
a) receive information regarding the topography of a field of arable land to be farmed and at least one physical parameter associated with the at least one drone and the at least one UAV,
b) receive information from the at least one drone and the at least one UAV regarding at least one of an amount of energy used and an amount of time taken by the at least one drone and the at least one UAV to traverse between at least two planting sites,
c) use linearly constrained integer quadratic programming to generate a time and/or energy optimized route plan for the at least one drone and the at least one UAV within the field, and
d) transmit the optimized route plan to the at least one drone and the at least one UAV using the wireless communication equipment.

11. The system of claim 10, wherein the autonomous farming control system comprises one or more low rank updates modules configured to receive the information from the at least one drone and the at least one UAV and the information regarding the topography of the field of arable land and convert the information into distance matrices $D_G$ and $D_A$.

12. The system of claim 11, wherein the autonomous farming control system comprises a linearly constrained integer quadratic programming (LCIQP) module configured to generate the optimized route plan for the at least one drone and the at least one UAV using the distance matrices $D_G$ and $D_A$ and at least one physical parameter associated with the at least one drone and the at least one UAV.

13. The system of claim 10, wherein the at least one drone is configured to plant seeds within the field or harvest a crop within the field.

14. The system of claim 10, wherein the at least one UAV is configured to deliver seed to the at least one drone and/or replace a battery pack carried by the at least one drone or providing fuel for an internal combustion engine of the at least one drone.

15. A method of autonomous farming using at least one ground-based drone and at least one unmanned aerial vehicle (UAV), the method comprising:
inputting information regarding the topography of a field of arable land to be farmed into an autonomous farming control system, the information including the identification of a plurality of planting sites within the field;
transmitting information from the at least one drone and the at least one UAV to the autonomous farming control system, the information comprising—
a) at least one of an amount of energy used and an amount of time taken by the at least one drone to traverse between planting sites p1 and p2 within the field, and
b) at least one of an amount of energy used and an amount of time taken by the at least one UAV to traverse between rendezvous sites x1 and x2 within the field;
converting, within one or more low rank updates modules of the autonomous farming control system, the information received from the at least one drone and the at least one UAV and the field topography information into distance matrices $D_G$ and $D_A$;
inputting the distance matrices $D_G$ and $D_A$ and at least one physical parameter associated with the at least one drone and the at least one UAV into a linearly constrained integer quadratic programming (LCIQP) module and outputting from the LCIQP module a time and/or energy optimized route plan for the at least one drone and the at least one UAV; and
transmitting instructions to the at least one drone and the at least one UAV for following the time and/or energy optimized route plans.

16. The method of claim 15, wherein sites p1, p2, x1, and x2 are independently selected sites within the field.

17. The method of claim 15, wherein x1 and x2 comprise points at which the at least one UAV rendezvouses with the at least one drone.

18. The method of claim 15, further comprising inputting into the autonomous farming control system information regarding soil conditions of the field and/or wind conditions within the field.

19. The method of claim 15, wherein the at least one physical parameter comprises at least one of a drone weight, a drone seed capacity, a UAV weight, a UAV seed capacity, an amount of seed required per planting site.

20. The method of claim 15, wherein the output from the LCIQP module comprises a planting matrix $P^D$ and a rendezvous matrix V, and wherein $P^D$ and $X^D$ are input to a post-processing module that generates the optimized route plan instructions for transmission to the at least one drone and the at least one UAV.

* * * * *